(12) United States Patent
Morita

(10) Patent No.: US 12,357,271 B2
(45) Date of Patent: Jul. 15, 2025

(54) ULTRASONIC PROBE, ULTRASONIC DIAGNOSTIC APPARATUS, AND METHOD FOR MANUFACTURING BACKING MATERIAL

(71) Applicant: Konica Minolta, Inc., Tokyo (JP)

(72) Inventor: Kiyokazu Morita, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 75 days.

(21) Appl. No.: 18/398,659

(22) Filed: Dec. 28, 2023

(65) Prior Publication Data

US 2024/0130711 A1  Apr. 25, 2024
US 2024/0225598 A9  Jul. 11, 2024

Related U.S. Application Data

(62) Division of application No. 17/060,900, filed on Oct. 1, 2020, now abandoned.

(30) Foreign Application Priority Data

Oct. 17, 2019  (JP) ................... 2019-190145

(51) Int. Cl.
*A61B 8/00* (2006.01)
*B06B 1/06* (2006.01)
*H10N 30/03* (2023.01)
*H10N 30/80* (2023.01)

(52) U.S. Cl.
CPC ............ *A61B 8/4444* (2013.01); *B06B 1/067* (2013.01); *H10N 30/03* (2023.02); *B06B 2201/76* (2013.01)

(58) Field of Classification Search
CPC ......... A61B 8/12; A61B 8/4444; A61B 8/445; A61B 8/4483; B06B 1/067; B06B 1/0674; B06B 2201/76; H10N 30/03
See application file for complete search history.

(56) References Cited

U.S. PATENT DOCUMENTS 7,105,986 B2    9/2006  Wildes et al.
2017/0164926 A1  6/2017  Spicci et al.

FOREIGN PATENT DOCUMENTS

JP  2009060501 A   3/2009
JP  2009261840 A   11/2009
JP  2017-527375 A  9/2017

OTHER PUBLICATIONS

R. Boubenia, et al, Metal composite as backing for ultrasonic transducers dedicated to non-destructive measurements in hostile, IOP Conf. Series: Materials Science and Engineering, 108, 2016, 10 pages.
Office Action issued on Jun. 27, 2023 for the related Japanese Application No. 2019-190145, with English translation, 6 pages.

*Primary Examiner* — Michael T Rozanski
(74) *Attorney, Agent, or Firm* — LUCAS & MERCANTI, LLP

(57) ABSTRACT

An ultrasonic probe includes: a piezoelectric element; and a backing material including a matrix resin and thermally conductive particles, arranged on one direction side with respect to the piezoelectric element, wherein a ratio of thermal conductivity of the backing material in a thickness direction to the thermal conductivity of the backing material in a horizontal direction is 3 or more.

3 Claims, 4 Drawing Sheets

50μm

50μm

ULTRASONIC PROBE, ULTRASONIC DIAGNOSTIC APPARATUS, AND METHOD FOR MANUFACTURING BACKING MATERIAL

CROSS REFERENCE TO RELATED APPLICATIONS

This application is a divisional of U.S. application Ser. No. 17/060,900 filed Oct. 1, 2020, which claimed the priority of Japanese Patent Application No. 2019-190145, filed on Oct. 17, 2019, and all applications are incorporated herein by reference in its entirety.

BACKGROUND

Technological Field

The present invention relates to an ultrasonic probe, an ultrasonic diagnostic apparatus, and a method for manufacturing a backing material.

Description of the Related Art

By simple operation of applying an ultrasonic probe connected to an ultrasonic diagnostic apparatus or communicable with the ultrasonic diagnostic apparatus to a body surface of a subject including human being and other animals or inserting the ultrasonic probe into the body, the ultrasonic diagnostic apparatus can obtain the shape, movement, or the like of a tissue as an ultrasonic diagnostic image. The ultrasonic diagnostic apparatus can repeatedly perform an examination advantageously because of high safety.

The ultrasonic probe incorporates, for example, a piezoelectric element that transmits and receives an ultrasonic wave. The piezoelectric element receives an electric signal (transmission signal) transmitted from the ultrasonic diagnostic apparatus, converts the received transmission signal into an ultrasonic signal to transmit the ultrasonic signal, receives an ultrasonic wave reflected in a living body to convert the ultrasonic wave into an electric signal (reception signal), and transmits the reception signal converted into the electric signal to the ultrasonic diagnostic apparatus.

In addition, the ultrasonic probe includes a backing material on the side opposite to a surface of the piezoelectric element facing a subject (note that hereinafter, regarding a member forming the ultrasonic probe, a surface facing an ultrasonic irradiation direction (surface facing a subject) is also referred to as "front surface", and a surface facing the direction opposite to the ultrasonic irradiation direction (surface opposite to the surface facing the subject) is also referred to as "back surface"). The backing material attenuates (including absorption/scattering) the ultrasonic wave transmitted from the piezoelectric element to a back surface side to suppress generation of noise (artifact) or the like due to reflection of the ultrasonic wave transmitted to the back surface side on an end surface of the backing material. In addition, the backing material dissipates heat from the piezoelectric element to the back surface side to suppress overheat or the like of an acoustic lens in contact with the subject due to heat generated in the piezoelectric element.

Therefore, various backing materials each having a higher thermal conductivity have been studied.

For example, JP 2017-527375 A discloses an ultrasonic probe including: a transducer assembly that can be operated so as to propagate ultrasonic energy; and a cooling system including a heat transfer device disposed so as to transfer heat generated by the transducer assembly. By inclusion of a graphene-based material or graphene to which another component such as a resin has been added in order to obtain a composite material in the heat transfer device, the ultrasonic probe has a favorable thermal conductivity.

However, as a result of studies of the present inventor, when it was tried to increase the thermal conductivity of a backing material by graphene described in JP 2017-527375 A, it was necessary to add a large amount of graphene to the backing material, it was difficult to make both mixing and moldability favorable, and desired thermally conductive performance of the backing material could not be obtained. In addition, when the backing material contains a large amount of graphene, an ultrasonic wave transmitted to a back surface side is not sufficiently attenuated disadvantageously.

SUMMARY

The present invention has been achieved in view of the above points, and an object of the present invention is to provide an ultrasonic probe including a backing material having high thermally conductive performance and favorable acoustic characteristics, an ultrasonic diagnostic apparatus including the backing material, and a method for preparing the backing material.

To achieve the abovementioned object, according to an aspect of the present invention, an ultrasonic probe reflecting one aspect of the present invention comprises: a piezoelectric element; and a backing material including a matrix resin and thermally conductive particles, arranged on one direction side with respect to the piezoelectric element, wherein a ratio of thermal conductivity of the backing material in a thickness direction to the thermal conductivity of the backing material in a horizontal direction is 3 or more.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, one or more embodiments of the present invention will be described with reference to the drawings. However, the scope of the invention is not limited to the disclosed embodiments.

1. Ultrasonic Probe

Figure 1:
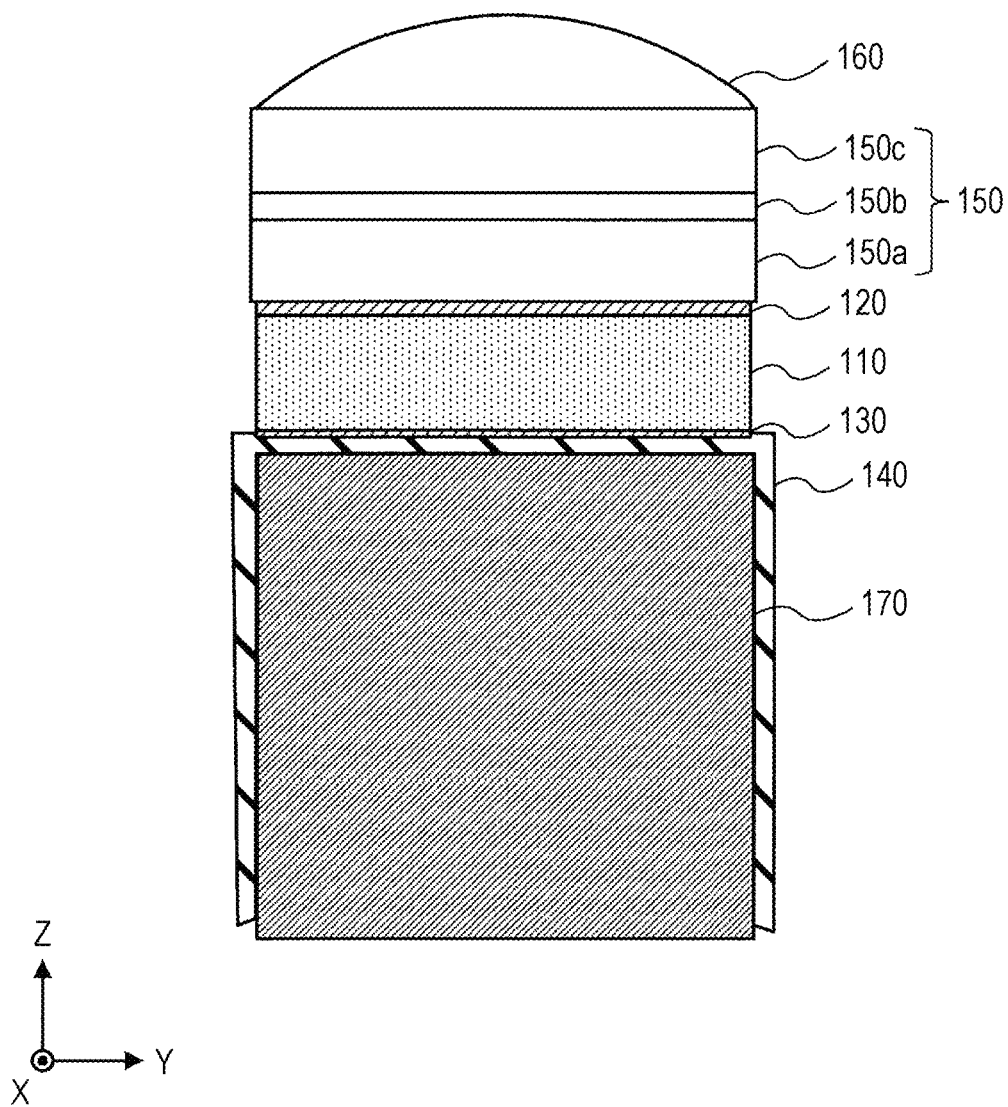
FIG. 1 is a cross-sectional view illustrating an example of an entire structure of an ultrasonic probe according to an embodiment of the present invention.

FIG. 1 is a cross-sectional view illustrating an example of an entire structure of an ultrasonic probe 100 according to an embodiment of the present invention.

As illustrated in FIG. 1, the ultrasonic probe 100 includes: a piezoelectric element 110; a ground electrode 120 disposed on a front surface side and a signal electrode 130 and a signal electric terminal 140 disposed on a back surface side for applying a voltage to the piezoelectric element 110; an acoustic matching layer 150 and an acoustic lens 160 disposed on the front surface side in this order from the piezoelectric element 110; and a backing material 170 disposed on the back surface side from the signal electric terminal 140.

1-1. Piezoelectric Element

The piezoelectric element 110 is formed by arranging a plurality of piezoelectric bodies (not illustrated) that transmits an ultrasonic wave by application of a voltage one-dimensionally in an X direction in FIG. 1. The thickness of the piezoelectric element 110 can be, for example, 0.05 mm or more and 0.4 mm or less. Each of the piezoelectric bodies is formed by a piezoelectric ceramic such as lead zirconate titanate (PZT), a piezoelectric single crystal such as lead magnesium niobate/lead titanate solid solution (PMN-PT) or lead zirconate niobate/lead titanate solid solution (PZN-PT), a composite piezoelectric body obtained by combining these materials and a polymer material, or the like. Note that the piezoelectric element 110 usually has a magnitude of an acoustic impedance of 10 to 30 MRayls.

1-2. Ground Electrode, Signal Electrode, and Signal Electric Terminal

The ground electrode 120 is an electrode disposed on a front surface of the piezoelectric element 110, and the signal electrode 130 is an electrode disposed on a back surface of the piezoelectric element 110. The ground electrode 120 and the signal electrode 130 can be formed by vapor-depositing or sputtering gold, silver, and the like, baking silver, or attaching a conductor such as copper to an insulating substrate and patterning the conductor. The signal electric terminal 140 is disposed in contact with a back surface side of the signal electrode 130, and connects the signal electrode 130 to an external power source or the like disposed in a main body 11 of the ultrasonic diagnostic apparatus 10. In the present embodiment, the signal electrode 130 is a flexible printed circuit (FPC) formed by attaching a conductor such as copper to an insulating substrate and patterning the conductor.

1-3. Acoustic Matching Layer

The acoustic matching layer 150 is a layer for matching acoustic characteristics between the piezoelectric element 110 and the acoustic lens 160, and is formed by a material having an acoustic impedance substantially intermediate between that of the piezoelectric element 110 and that of the acoustic lens 160. In the present embodiment, the acoustic matching layer 150 includes three layers of a first acoustic matching layer 150a, a second acoustic matching layer 150b, and a third acoustic matching layer 150c.

Here, the first acoustic matching layer 150a is formed by a material such as graphite impregnated with silicon, quartz, free-machining ceramics, or metal, graphite filled with metal particles, or an epoxy resin filled with a filler such as metal or an oxide, having an acoustic impedance of 8 MRayls or more and 20 MRayls or less. The second acoustic matching layer 150b is formed by graphite or an epoxy resin filled with a filler such as metal or an oxide, having an acoustic impedance of 3 MRayls or more and 8 MRayls or less. The third acoustic matching layer 150c is formed by a plastic material mixed with a rubber material, a resin filled with a silicone rubber, or the like, having an acoustic impedance of 1.9 MRayls or more and 2.3 MRayls or less.

By making the acoustic matching layer 150 multilayered in this way, the band of the ultrasonic probe can be widened. Note that when the acoustic matching layer 150 is multilayered, the acoustic impedance of each layer is more preferably set such that the acoustic impedance of the acoustic matching layer 150 approaches the acoustic impedance of the acoustic lens 160 stepwise or continuously as the acoustic matching layer 150 is closer to the acoustic lens 160. In addition, the layers of the multilayered acoustic matching layer 150 may be bonded to each other with an adhesive usually used in the present technical field, such as an epoxy-based adhesive.

Note that the material of the acoustic matching layer 150 is not limited to the above materials, and may be aluminum, an aluminum alloy (for example, an AL-Mg alloy), a magnesium alloy, macor glass, glass, fused quartz, copper graphite, polyethylene (PE), polypropylene (PP), polycarbonate (PC), an ABC resin, an ABS resin, an AAS resin, an AES resin, nylon (PA6 or PA6-6), polyphenylene oxide (PPO), polyphenylene sulfide (PPS: PPS containing glass fiber is also available), polyphenylene ether (PPE), polyether ether ketone (PEEK), polyamide imide (PAI), polyethylene terephthalate (PETP), an epoxy resin, a urethane resin, or the like. A material obtained by adding zinc oxide, titanium oxide, silica, alumina, red iron oxide, ferrite, tungsten oxide, yttrium oxide, barium sulfate, tungsten, molybdenum, or the like as a filler to a thermosetting resin such as an epoxy resin and molding the resulting mixture is preferable.

1-4. Acoustic Lens

The acoustic lens 160 is formed by a polymer material or the like having an acoustic impedance close to that of a living body and having a sound velocity different from that of the living body, and focuses ultrasonic waves transmitted from the piezoelectric element 110 using refraction due to a difference in sound velocity between the living body and the acoustic lens 160 to improve resolution. In the present embodiment, the acoustic lens 160 is a cylindrical acoustic lens extending in a Y direction (direction orthogonal to an arrangement direction X of the piezoelectric bodies) in the drawing and having a convex shape in a Z direction. The acoustic lens 160 focuses the ultrasonic waves in the Y direction and emits the ultrasonic waves to the outside of the ultrasonic probe 100.

The acoustic lens 160 may be, for example, a homopolymer such as a known silicone-based rubber, a butadiene-based rubber, a polyurethane rubber, or an epichlorohydrin rubber, or a copolymer rubber such as an ethylene-propylene copolymer rubber obtained by copolymerizing ethylene and propylene. Among these materials, the silicone-based rubber and the butadiene-based rubber are preferably used.

Examples of the silicone-based rubber include a silicone rubber and a fluoro silicone rubber. The silicone rubber refers to an organopolysiloxane having a molecular skeleton formed by Si—O bonds, in which a plurality of organic groups is mainly bonded to the Si atoms. Usually, a main component of the organopolysiloxane is methyl polysiloxane, and 90% or more of all the organic groups are methyl groups. A substance into which a hydrogen atom, a phenyl group, a vinyl group, an allyl group, or the like is introduced instead of a methyl group can also be used. The silicone rubber can be obtained, for example, by kneading a curing agent (vulcanizing agent) such as benzoyl peroxide with an organopolysiloxane having a high polymerization degree, and heating and vulcanizing the kneaded product to cure the kneaded product. If necessary, an organic or inorganic filler such as silica or nylon powder, a vulcanization aid such as sulfur or zinc oxide, or the like may be added.

Examples of the butadiene-based rubber include a polymer rubber obtained by polymerizing butadiene alone and a copolymer rubber obtained by copolymerizing butadiene as a main component with a small amount of styrene or acrylonitrile. The butadiene rubber is a synthetic rubber obtained by polymerizing butadiene having a conjugated double bond. The butadiene rubber can be obtained by 1.4-polymerizing or 1.2-polymerizing butadiene alone having a conjugated double bond. The butadiene rubber may be vulcanized with sulfur or the like.

Examples of a commercially available silicone rubber include: KE742U, KE752U, KE931U, KE941U, KE951U, KE961U, KE850U, KE555U, and KE575U (all of which are manufactured by Shin-Etsu Chemical Co., Ltd.); TSE221-3U, TE221-4U, TSE2233U, XE20-523-4U, TSE27-4U, TSE260-3U, and TSE-260-4U (all of which are manufactured by Momentive Performance Materials Inc.); and SH35U, SH55UA, SH831U, SE6749U, SE1120U, and SE4704U (all of which are manufactured by Toray Dow Corning Co. Ltd.).

1-5. Backing Material

The backing material 170 is a layer that holds the piezoelectric element 110, simultaneously attenuates an ultrasonic wave transmitted from the piezoelectric element 110 to a back surface side, and releases heat generated from the piezoelectric element 110 to the back surface side. Examples of a base material (matrix resin) of the backing material 170 include a natural rubber, a ferrite rubber, an epoxy resin, polyvinyl chloride, polyvinyl butyral (PVB), an ABS resin, polyurethane (PUR), polyvinyl alcohol (PVAL), polyethylene (PE), polypropylene (PP), polyacetal (POM), polyethylene terephthalate (PETP), fluororesin (PTFE) polyethylene glycol, a polyethylene terephthalate-polyethylene glycol copolymer, and other thermoplastic resins. Among the above base materials (matrix resins), the epoxy resin is preferable.

Examples of the epoxy resin include a novolac type epoxy resin such as a bisphenol A type, a bisphenol F type, a resole novolac type, or a phenol modified novolac type, a polycyclic aromatic epoxy resin such as a naphthalene structure-containing type, an anthracene structure-containing type, or a fluorene structure-containing type, a hydrogenated alicyclic epoxy resin, a liquid crystalline epoxy resin, and a powder epoxy resin.

The matrix resin contained in the backing material 170 according to the present embodiment is preferably made of a powder resin. The matrix resin is preferably made of powder particles having a number average particle size of 10 μm or more and 200 μm or less, more preferably powder particles having a number average particle size of 10 μm or more and 100 μm or less, still more preferably powder particles having a number average particle size of 30 μm or more 70 μm or less. The shape of the backing material 170 is not particularly limited as long as being able to attenuate a transmitted ultrasonic wave.

Figure 2A:
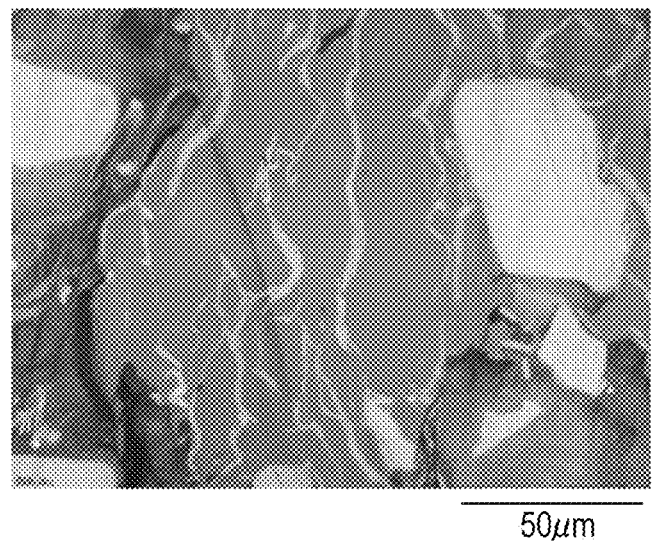
FIG. 2A is a cross-sectional view of a backing material of the ultrasonic probe according to the embodiment of the present invention.
Figure 2B:
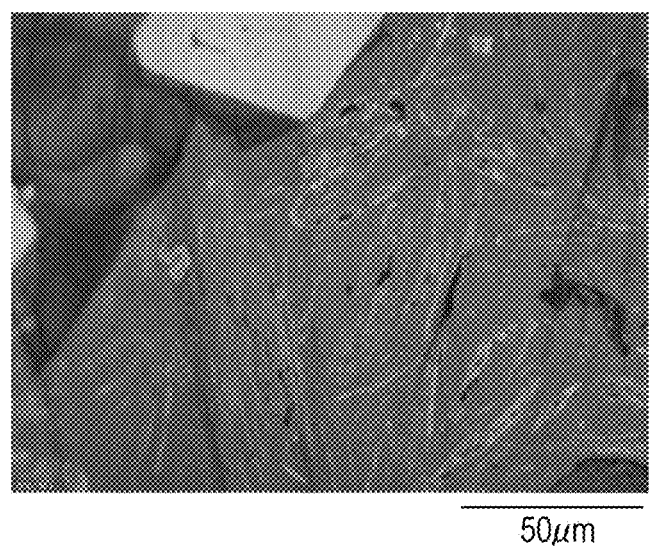
FIG. 2B is a cross-sectional view of a backing material of an ultrasonic probe of Comparative Example.

As illustrated in FIG. 2A, thermally conductive particles included in the backing material 170 according to the present embodiment are oriented in the thickness direction of the backing material 170. Here, the thickness direction of the backing material means a direction perpendicular to a surface facing an ultrasonic irradiation direction (surface facing a subject) with a surface facing the direction opposite to the ultrasonic irradiation direction (surface opposite to the surface facing the subject) as a bottom surface. In addition, "oriented" means that the thermally conductive particles are aggregated and arranged in the thickness direction of the backing material. In addition, aggregation means that a plurality of thermally conductive particles gathers to form a stripe. Meanwhile, thermally conductive particles included in a backing material of an ultrasonic probe of Comparative Example illustrated in FIG. 2B are dispersed in the backing material without being oriented.

When the resin is made of powder, the powder particles of the resin can be arranged along an interface (surface) of the thermally conductive particles. Therefore, the thermally conductive particles in the backing material pressurized during molding can be oriented in the thickness of the backing material. In addition, the backing material can have a region where the thermally conductive particles are aggregated and a region where the thermally conductive particles are not aggregated. As a result, the orientation of the thermally conductive particles can be improved. Therefore, the thermal conductivity of the backing material can be improved to 30 W/mk in the thickness direction and 6 W/mk in the horizontal direction.

In addition, a ratio of the thermal conductivity of the backing material 170 according to the present embodiment in the thickness direction to the thermal conductivity thereof in the horizontal direction is preferably 3 or more and 10 or less, and more preferably 4 or more and 5 or less. If the ratio of the thermal conductivity of the backing material 170 in the thickness direction to the thermal conductivity thereof in the horizontal direction is 3 or more, even when the temperature inside the ultrasonic probe 100 rises to about 50 to 60° C. during use of the ultrasonic probe 100, heat can be quickly dissipated from the direction opposite to a subject side. Note that the thermal conductivity of the backing material according to the present embodiment in each of the thickness direction and the horizontal direction can be measured by a laser flash method according to JIS R1611: 2010.

The backing material 170 enhances the thermal conductivity by containing the thermally conductive particles.

A ratio of the sound velocity of the backing material 170 according to the present embodiment in the thickness direction to the sound velocity thereof in the horizontal direction is preferably 0.5 or more, and more preferably 0.6 or more and 1.0 or less. By setting the ratio of the sound velocity of the backing material 170 in the thickness direction to the sound velocity thereof in the horizontal direction to 0.6 or more, it is possible to suppress anisotropy and to obtain not only desired thermally conductive performance but also desired attenuation. In addition, by setting the ratio of the sound velocity of the backing material 170 in the thickness direction to the sound velocity thereof in the horizontal direction to 1.0 or less, it is possible to suppress an increase in only one function (for example, thermally conductive performance). Note that the sound velocity of the backing material 170 in each of the thickness direction and the horizontal direction can be determined according to JIS Z2353:2003.

The attenuation of the backing material 170 according to the present embodiment is preferably 9 dB/mm·MHz or more, and the acoustic impedance thereof is preferably 1.5 to 3.0 Mrayls.

1-5-1. Thermally Conductive Particles

The thermally conductive particle contain a thermally conductive material. The thermally conductive material has a thermal conductivity of preferably 60 to 5000 w/mk, more preferably 200 to 3000 w/mk, still more preferably 400 to 3000 w/mk from a viewpoint of easily adjusting acoustic characteristics while further enhancing the thermally conductive performance of the backing material 170. Examples of the thermally conductive material having a thermal conductivity within the above range include aluminum oxide, silicon carbide, aluminum nitride, silicon nitride, beryllium oxide, boron nitride, magnesium oxide, graphene, a carbon nanotube, aluminum, gold, silver, iron, and copper. The thermally conductive particles may contain one or more kinds selected from these thermally conductive materials. In addition, the thermally conductive particles may contain a material other than the above thermally conductive materials, like composite particles described later.

Here, a state in which the backing material 170 has favorable acoustic characteristics means that the attenuation ratio of an ultrasonic wave by the backing material 170 is sufficiently high, the backing material 170 has a sound velocity suitable for measurement, or the backing material 170 has an acoustic impedance to such an extent that the backing material 170 can appropriately reflect an ultrasonic wave transmitted from the piezoelectric element 110. Note that more preferably, the attenuation ratio of an ultrasonic wave by the backing material 170 is sufficiently high, and the backing material 170 has an acoustic impedance to such an extent that the backing material 170 can appropriately reflect an ultrasonic wave transmitted from the piezoelectric element 110.

Here, the attenuation ratio of an ultrasonic wave is preferably higher from a viewpoint of suppressing generation of noise (artifact). When a better-shaped waveform is desired even if sensitivity is sacrificed to some extent, a value of the acoustic impedance can be increased. When the sensitivity is desired to be increased, the value of the acoustic impedance can be decreased. In addition, the shape of a band can also be controlled by the value of the acoustic impedance. When the value of the acoustic impedance is low, the band is wide. When the value of the acoustic impedance is high, the band is narrow.

The thermally conductive material is preferably multilayer (ML) graphene, silicon carbide, or a carbon nanotube from a viewpoint of adjusting the orientation state of the thermally conductive particles to easily adjust the acoustic characteristics.

Note that the orientation state of the thermally conductive particles is preferably adjusted such that aggregation of the thermally conductive particles in the backing material 170 is suppressed. As a result, it is possible to suppress a variation in the thermal conductivity and acoustic characteristics of the backing material 170, to enhance the thermally conductive performance of the backing material 170, and to improve the acoustic characteristics.

In addition, when the amount of the thermally conductive particles contained in the backing material 170 is large, the durability of the backing material 170 is likely to decrease, or the acoustic impedance of the backing material 170 is likely to deviate from the suitable range.

Note that the amount of the thermally conductive particles contained in the backing material 170 is preferably smaller, while the backing material 170 preferably contains the thermally conductive particles in such an amount that overheat of the acoustic lens 160 can be suppressed from a viewpoint of suppressing aggregation of the thermally conductive particles. Specifically, by containing the thermally conductive particles, the backing material 170 has a thermal conductivity of preferably 2.0 W/mk or more, more preferably 4.0 W/mk or more, still more preferably 10.0 W/mk or more, particularly preferably 20.0 W/mk or more.

However, according to finding of the present inventor, by simply increasing the amount of the thermally conductive particles contained in the backing material 170, the thermally conductive particles are more easily aggregated, and therefore the thermal conductivity of the backing material 170 does not rise as expected. In order to efficiently enhance the thermal conductivity of the backing material 170, it is necessary to adjust the orientation state of the thermally conductive particles to disperse the thermally conductive particles more suitably. In the present invention, by using the matrix resin made of a powder resin, due to an excluded volume effect of particles such as the thermally conductive particles contained in the backing material, the thermally conductive particles can be oriented at regular intervals even if the thermally conductive particles are not uniformly dispersed at the time of mixing. As a result, the thermal conductivity of the backing material can be improved up to 30 W/mk in the thickness direction and up to 6 W/mk in the horizontal direction.

In addition, the thermally conductive particles have a number average particle size of preferably 10 μm or more and 150 μm or less, more preferably 10 μm or more and 100 μm or less from a viewpoint of easily adjusting the orientation state of the thermally conductive particles. When the number average particle size of the thermally conductive particles is within the above range, the thermally conductive particles are more easily dispersed, and the orientation state of the thermally conductive particles is more easily adjusted as compared with a case of using particles having a smaller number average particle size. Note that here, the number average particle size of particles is a value measured using a laser particle size distribution measuring device. Alternatively, here, the number average particle size of the particles contained in the backing material 170 may be a value obtained by thinly cutting the backing material 170, imaging the cut backing material 170 with a transmission electron microscope at a magnification of about 1,000,000 times, and analyzing the obtained image with well-known analysis software.

1-5-2. Composite Particles

The thermally conductive particles may be composite particles from a viewpoint of suppressing aggregation of the thermally conductive particles to easily adjust the orientation state of the thermally conductive particles. By using the composite particles, a particle concentration in an epoxy resin can be reduced, and therefore a particle surface is easily covered with the epoxy resin. This can suppress generation of bubbles and cracks during molding of the backing material 170, and can suppress a change in capacity during dicing.

The composite particles are obtained by combining particles made of the above-described thermally conductive material with a material other than the thermally conductive material (for example, an elastomer). The composite particles may further contain a filler and the like.

The elastomer is a substance having rubber elasticity at room temperature. The elastomer may be a thermosetting elastomer or a thermoplastic elastomer.

Examples of the thermoplastic elastomer include a polyester elastomer, a polyamide elastomer, a polyether elastomer, a polyurethane elastomer, a polyolefin elastomer, a polystyrene elastomer, a polyacrylic elastomer, a polydiene elastomer, a silicone-modified polycarbonate elastomer, and a fluorine copolymer elastomer.

Examples of the thermosetting elastomer include a flexible epoxy resin, a silicone resin, an isoprene rubber, an ethylene propylene rubber, a butadiene rubber, a chloroprene rubber, and a natural rubber.

Since the ultrasonic probe is sterilized in a high temperature gas environment or the like, the elastomer is preferably a thermosetting elastomer that is unlikely to be deformed or flown by a change in temperature, and is more preferably a silicone resin.

The composite particles can be manufactured by pulverizing a mixture of materials of the composite particles with a pulverizer. At this time, the elastomer is preferably a material having a short elongation at break and a lower hardness from a viewpoint of easily pulverizing the mixture to facilitate manufacture of the composite particles, and from a viewpoint of suppressing generation of bubbles and cracks due to damage of the composite particles during molding of the backing material 170.

Note that pulverization of the composite particles may be pulverization at room temperature or freeze pulverization. An impact type pulverizer such as a turbo mill, a pin mill, a hammer mill, or a Linrex mill can be used for pulverizing the composite particles. In the freeze pulverization, the composite particles are cooled to a temperature equal to or lower than an embrittlement point in a liquid nitrogen (about −196° C.) atmosphere, and then pulverization can be performed using the impact type pulverizer. When the composite particles contain a large amount of flexible components (for example, a silicone resin), the freeze pulverization can cool the composite particles to a temperature equal to or lower than the glass transition temperature (Tg) of the silicone resin, and therefore can easily pulverize the composite particles.

The elastomer has a tensile breaking strength of preferably 3.0 MPa or less, more preferably 1.5 MPa or less from the above viewpoint. The elastomer has a tensile breaking elongation of preferably 160% or less, more preferably 140% or less from the above viewpoint. The tensile breaking strength and tensile breaking elongation of the elastomer can be values obtained by measurement according to JIS K 6251 (2017). A lower limit value of the tensile breaking elongation is not particularly limited, but can be 30% or more.

The elastomer has a hardness of preferably 38 or less, more preferably 32 or less, as measured by a type A durometer, from the above viewpoint. The hardness of the elastomer can be a value obtained by measurement according to JIS K 6253-1 (2012).

The elastomer has an adhesive strength of preferably 0.3 MPa or more, more preferably 0.5 MPa or more from a viewpoint of suppressing generation of two peaks of the particle size by peeling of the elastomer from other materials (thermally conductive material and filler) in shearing during pulverization. The adhesive strength of the elastomer can be a value obtained by measurement according to JIS K 6256-1 (2013).

The elastomer preferably contains a coupling agent such as a silane coupling agent, a titanium coupling agent, or an aluminum coupling agent from a viewpoint of further enhancing adhesiveness with the other materials to suppress generation of two peaks of the particle size by the peeling. When the elastomer is a silicone resin (particularly room temperature vulcanizing (RTV) silicone resin), the coupling agent preferably has a double bond in a molecule thereof from a viewpoint of further enhancing the adhesiveness with the other materials.

Examples of a commercially available product of the silane coupling agent include KBM-1003, KBM-1403, KBM-502, KBM-503, KBE-1003, KBE502, KBE-503, and KBM-5103 (all of which are manufactured by Shin-Etsu Chemical Co., Ltd.). Examples of a commercially available product of the titanium coupling agent include: Plenact 55 and Plenact TTS (both of which are manufactured by Ajinomoto Fine-Techno Co., Inc., "Plenact" is a registered trademark of Ajinomoto Co., Inc.); and Orgatix TC-100, Orgatix TC-401, Orgatix TC-710, and Orgatix TC-120 (all of which are manufactured by Matsumoto Fine Chemical Co., Ltd., "Orgatix" is a registered trademark of Matsumoto Fine Chemical Co., Ltd.). Examples of a commercially available product of the aluminum coupling agent include Plenact AL-M (manufactured by Ajinomoto Fine-Techno Co., Inc.).

The elastomer preferably has a specific gravity of 1.1 or less from a viewpoint of increasing a difference in density between the elastomer and the filler to increase the attenuation ratio of an ultrasonic wave by the composite particles. By combining such an elastomer with tungsten oxide (specific gravity: 7.16) or thermal expansion microcapsules (specific gravity of commercial product: for example, 0.03), it is easier to cause scattering of an ultrasonic wave at an interface between the elastomer and the filler to further increase the attenuation ratio of an ultrasonic wave by the composite particles.

Examples of the filler include inorganic particles and hollow particles. Examples of the inorganic particles include ferrite, tungsten oxide, yttrium oxide, bismuth oxide, zinc oxide, zirconium oxide, tin oxide, nickel oxide, barium oxide, manganese oxide, yttrium oxide, indium oxide, tantalum oxide, and barium titanate.

Examples of the hollow particles include glass balloons, hollow silica, cenolite, phenol resin microballoons, urea resin microballoons, polymethylmethacrylate balloons, and thermal expansion microcapsules. The filler may be used singly or in combination of two or more kinds thereof.

The composite particles can be prepared by various known methods.

The thermally conductive particles that are the composite particles have a density of preferably 1.0 to 3.5 g/cm$^3$, more preferably 1.5 to 3.0 g/cm$^3$. When the density of the composite particles is within the above range, it is easy to control the acoustic impedance of the backing material within a desired range even when the amount of the composite particles added is small.

The thermally conductive particles that are the composite particles have a number average particle size of preferably 100 to 500 μm, more preferably 150 to 300 μm. When the number average particle size of the thermally conductive particles is within the above range, the thermally conductive particles are more easily dispersed, and the orientation state of the thermally conductive particles is more easily adjusted as compared with a case of using particles having a smaller number average particle size.

1-5-3. Non-Thermally Conductive Particles

The backing material 170 may contain non-thermally conductive particles in addition to the thermally conductive particles from a viewpoint of adjusting the orientation state of the thermally conductive particles to easily adjust the acoustic characteristics. In particular, when the backing material 170 contains non-thermally conductive particles having a relatively large particle size, the thermally conductive particles can be oriented along an interface of the non-thermally conductive particles. As a result, a heat transfer path is formed by the thermally conductive particles, and the thermal conductivity of the backing material 170 can be efficiently enhanced even if the amount of the thermally conductive particles is small. In addition, this suppresses agglomeration of the thermally conductive particles and also suppresses a variation in the acoustic characteristics of the backing material 170. In addition, by orienting the thermally conductive particles along an interface of the non-thermally conductive particles, it is possible to suppress formation of an aggregate of the thermally conductive particles. Therefore, it is possible to suppress generation of bubbles and cracks during molding of the backing material 170, to improve the durability of the backing material 170, and to suppress a change in capacity during dicing. Note that the non-thermally conductive particles have a number average particle size of preferably 100 to 350 μm, more preferably 150 to 260 μm.

The non-thermally conductive particles are preferably composite particles from a viewpoint of easily adjusting the acoustic characteristics of the backing material 170.

The non-thermally conductive particles that are composite particles can have a similar configuration to the above-described thermally conductive particles that are composite particles except for containing no thermally conductive material.

1-5-4. Base Material (Matrix Resin)

The backing material 170 contains a matrix resin as a base material.

The matrix resin may be a thermosetting resin such as a synthetic rubber, a natural rubber, or an epoxy resin, or may be a thermoplastic resin such as polyethylene or nylon. The matrix resin is preferably an epoxy resin or nylon.

Examples of the epoxy resin include a bisphenol type epoxy resin such as a bisphenol A type or a bisphenol F type, a novolac type epoxy resin such as a resole novolac type or a phenol modified novolac type, a polycyclic aromatic epoxy resin such as a naphthalene structure-containing type, an anthracene structure-containing type, or a fluorene structure-containing type, a hydrogenated alicyclic epoxy resin, and a liquid crystalline epoxy resin. The epoxy resin may be used singly or in combination of two or more kinds thereof. Examples of the nylon include nylon 6, nylon 11, nylon 12, and nylon 66.

The epoxy resin or nylon, which is a raw material of the matrix resin, is preferably in a form of powder particles. By using the matrix resin made of powder particles, due to an excluded volume effect of particles such as the thermally conductive particles contained in the backing material, the powder particles can be arranged along an interface (surface) of the thermally conductive particles. As a result, the thermally conductive particles can be oriented at regular intervals even if the thermally conductive particles are not uniformly dispersed at the time of mixing. Furthermore, by pressurization during molding, the orientation of the thermally conductive particles can be improved. As a result, the thermal conductivity of the backing material can be improved up to 30 W/mk in the thickness direction and up to 6 W/mk in the horizontal direction.

The matrix resin has a glass transition temperature (Tg) of preferably 30° C. or higher and 200° C. or lower, more preferably 50° C. or higher and 150° C. or lower, still more preferably 60° C. or higher and 100° C. or lower. When the glass transition temperature (Tg) of the thermosetting resin is 80° C. or higher, even if the temperature inside the ultrasonic probe 100 rises to about 50° C. to 60° C. during use of the ultrasonic probe 100, the thermosetting resin can maintain a predetermined hardness. Therefore, deformation of the backing material 170 due to softening of the base material can be suppressed. When the glass transition temperature (Tg) of the thermosetting resin is 200° C. or lower, the backing material 170 can be hardened to such an extent that the backing material 170 is easily cut during processing of the backing material 170, and the brittleness of the backing material 170 can be reduced to such an extent that the backing material 170 is not damaged during cutting of the backing material 170.

Note that the content of the matrix resin in the backing material 170 is preferably 40% by volume or more and 64% by volume or less with respect to the total volume of the backing material 170.

2. Method for Preparing Backing Material

The backing material 170 can be prepared by a method including a step of mixing a raw material of the matrix resin, the thermally conductive resin, and a non-thermally conductive material to prepare a mixture, and a step of molding the mixture.

The mixture may contain the raw material of the matrix resin, the thermally conductive material, the non-thermally conductive material, and other additives at a ratio according to the above-described configuration of the backing material 170.

Alternatively, the mixture may contain the raw material of the matrix resin, the thermally conductive resin, and the non-thermally conductive material.

Alternatively, the mixture may contain the raw material of the matrix resin in a form of powder and the thermally conductive resin.

The matrix resin is preferably made of powder particles having a number average particle size of 10 μm or more and 200 μm or less, more preferably powder particles having a number average particle size of 10 μm or more and 100 μm or less, still more preferably powder particles having a number average particle size of 30 μm or more 70 μm or less. By making the number average particle size of the raw material of the matrix resin smaller than that of the composite particles to be added as the thermally conductive material, it is possible to suppress cracking during molding, and to completely fill a gap between the particles when the raw material is melted.

When the raw material of the matrix resin is in a form of powder, the powder particles of the resin can be arranged along an interface (surface) of the thermally conductive particles. Therefore, the thermally conductive particles in the backing material pressurized during molding can be oriented in the thickness of the backing material. In addition, the backing material can have a region where the thermally conductive particles are aggregated and a region where the thermally conductive particles are not aggregated. As a result, the orientation of the thermally conductive particles can be improved. Therefore, the thermal conductivity of the backing material can be improved to 30 W/mk in the thickness direction and 6 W/mk in the horizontal direction.

When the raw material of the matrix resin is in a form of powder, the sufficiently mixed mixture is put in a die and heated while being pressurized in the thickness direction under vacuum deaeration, and the mixture can be thereby molded into the shape of the backing material 170.

When the raw material of the matrix resin is in a form of liquid, the liquid raw material is poured into a die, sufficiently defoamed, stirred, and then heated, and the mixture can be thereby molded into the shape of the backing material 170.

Note that when the raw material of the matrix resin is a thermosetting resin, a curing agent is preferably added to the mixture. Examples of the curing agent include: a chain aliphatic polyamine such as diethylenetriamine, triethylenetetramine, dipropylenediamine, or diethylaminopropylamine; a cyclic aliphatic polyamine such as N-aminoethylpiperazine, mensendiamine, or isophoronediamine; an aromatic amine such as m-xylenediamine, metaphenylenediamine, diaminodiphenylmethane, or diaminodiphenylsulfone; a polyamide resin; a secondary amine or a tertiary amine such as piperidine, N,N-dimethylpiperazine, triethylenediamine, 2,4,6-tris(dimethylaminomethyl) phenol, benzyldimethylamine, or 2-(dimethylaminomethyl) phenol; an imidazole such as 2-methylimidazole, 2-ethylimidazole, or 1-cyanoethyl-2-undecylimidazolium trimellitate; a liquid polymercaptan and a polysulfide; and an acid anhydride such as phthalic anhydride, trimellitic anhydride, methyltetrahydrophthalic anhydride, methylendomethylenetetrahydrophthalic anhydride, methylbutenyltetrahydrophthalic anhydride, or methylhexahydrophthalic acid. The curing agent may be used singly or in combination of two or more kinds thereof.

3. Ultrasonic Diagnostic Apparatus

Figure 3:
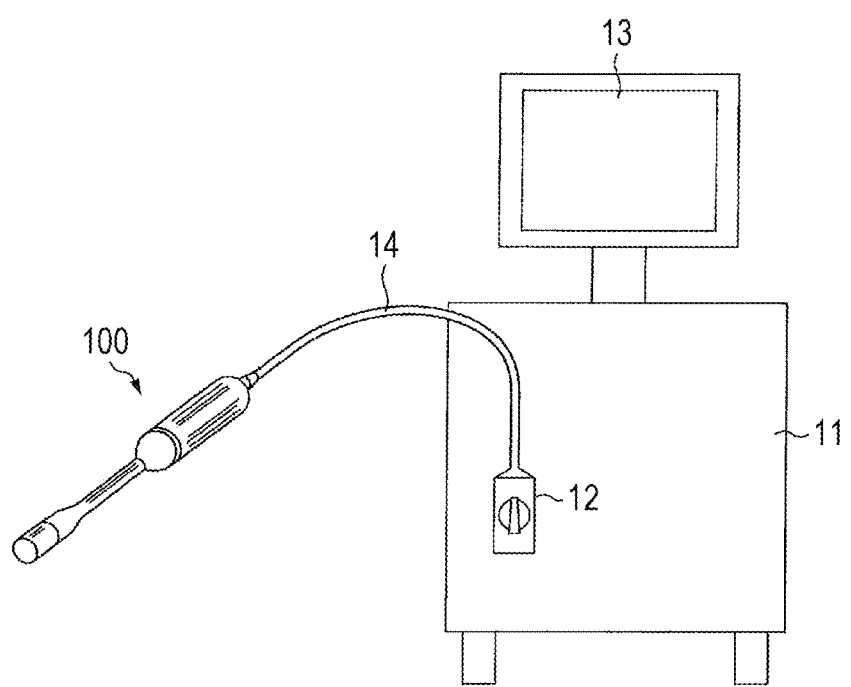
FIG. 3 is a schematic view illustrating an example of an ultrasonic diagnostic apparatus including the ultrasonic probe according to the embodiment of the present invention.

FIG. 3 is a schematic view illustrating an example of the ultrasonic diagnostic apparatus 10 including the ultrasonic probe 100. The ultrasonic diagnostic apparatus 10 includes the ultrasonic probe 100, the main body 11, a connector 12, and a display 13.

The ultrasonic probe 100 is connected to the ultrasonic diagnostic apparatus 10 via a cable 14 connected to the connector 12.

An electric signal (transmission signal) transmitted from the ultrasonic diagnostic apparatus 10 is transmitted to the piezoelectric element 110 of the ultrasonic probe 100 via the cable 14. The transmission signal is converted into an ultrasonic wave in the piezoelectric element 110 and transmitted into a living body. The transmitted ultrasonic wave is reflected by a tissue or the like in the living body. A part of the reflected wave is received again by the piezoelectric element 110, converted into an electric signal (reception signal), and transmitted to the main body 11 of the ultrasonic diagnostic apparatus 10. The reception signal is converted into image data in the main body 11 of the ultrasonic diagnostic apparatus 10 and displayed on the display 13.

The ultrasonic diagnostic apparatus according to the embodiment of the present invention includes the ultrasonic probe according to the embodiment of the present invention, and therefore can generate an ultrasonic image with favorable image quality.

EXAMPLES

Hereinafter, the present invention will be described more specifically using the following tests, but the present invention is not limited to the following tests.

1. Preparation of Composite Particles

Using the following materials, non-thermoplastic particles that were composite particles and thermoplastic particles that were composite particles were prepared.

(Elastomer)
Main agent 1: TSE3032(A) (manufactured by Momentive Performance Materials, Inc., thermosetting liquid silicone rubber)
Curing agent 1: TSE3032(B) (manufactured by Momentive Performance Materials, Inc.)
Main agent 2: TSE3033(A) (manufactured by Momentive Performance Materials, Inc., thermosetting liquid silicone rubber)
Curing agent 2: TSE3033(B) (manufactured by Momentive Performance Materials, Inc.)

(Filler)
Filler 1: A2-WO$_3$ (number average particle size: 7 to 12 μm, manufactured by A.L.M.T Corp., tungsten trioxide powder)
Filler 2: C3-WO$_3$ (number average particle size: 15 to 20 μm, manufactured by A.L.M.T Corp., tungsten trioxide powder)
Filler 3: Expancel 920DE40d30 (number average particle size: 35 to 55 μm, manufactured by Japan Fillite Co., Ltd., thermal expansion microcapsules)

Note that an elastomer obtained by a reaction between main agent 1 and curing agent 1 has
a tensile breaking strength of 4.5 MPa, measured according to JIS K 6251 (2017), a tensile breaking elongation of 210%, measured according to JIS K 6251 (2017), and a hardness of 35, measured by a type A durometer.

An elastomer obtained by a reaction between main agent 2 and curing agent 2 has a tensile breaking strength of 1.0 MPa, measured according to JIS K 6251 (2017), a tensile breaking elongation of 130%, measured according to JIS K 6251 (2017), and a hardness of 30, measured by a type A durometer.

(Particles Made of Thermally Conductive Material)
Particles 1: iGrafen-α (number average particle size: 100 μm, manufactured by ITEC Co., Ltd., multilayer graphene)

1-1. Composite Particles 1

To 100 parts by mass of main agent 1, 803 parts by mass of filler 1 was added, and the resulting mixture was sufficiently mixed with a vacuum mixer "ARV-310" (manufactured by Thinky Corporation). Subsequently, 10 parts by mass of curing agent 1 was added thereto and mixed well to obtain mixture 1.

Mixture 1 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 1. Block 1 had a density of 4.07 g/cm$^3$. Block 1 was cut into cubes each having a side length of 1 cm, and roughly pulverized at room temperature with a cutter mill "VM-20" (manufactured by Makino MFG. Co., Ltd.). Thereafter, the resulting product was finely pulverized with a pin mill "M-4" (manufactured by Nara Machinery Co., Ltd.) using a screen of 0.5 mm at a rotation speed of 2800 rpm. Finally, the resulting product was sieved with a circular vibrating screener "KG-400" (manufactured by Nishimura Machine Works Co., Ltd., mesh size 212 μm) to obtain composite particles 1 which were non-thermally conductive particles.

Using a laser type particle size distribution measuring device (LMS-30 (manufactured by Seishin Enterprise Co., Ltd.)), the particle size distribution of composite particles 1 was measured under stirring and ultrasonic dispersion by using isopropyl alcohol as a measurement dispersion medium and adjusting an optimum point of scattering intensity. As a result of measuring the particle sizes, the number average particle size was 112 μm.

1-2. Composite Particles 2

To 50 parts by mass of main agent 2, 365 parts by mass of filler 2 and 0.91 parts by mass of filler 3 were added, and the resulting mixture was sufficiently mixed with a vacuum mixer. Subsequently, 50 parts by mass of curing agent 2 was added thereto and mixed well to obtain mixture 2.

Mixture 2 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 2. Block 2 had a density of 2.29 g/cm$^3$. Block 2 was cut into cubes each having a side length of 1 cm, and roughly pulverized at room temperature with the cutter mill. Thereafter, the resulting product was finely pulverized with the pin mill using a screen of 0.5 mm at a rotation speed of 2800 rpm. Finally, the resulting product was sieved with the circular vibrating screener (mesh size 212 μm) to obtain composite particles 2 which were non-thermally conductive particles. As a result of measuring the number average particle size in a similar manner to the composite particles 1, the number average particle size was 245 μm.

1-3. Composite Particles 3

To 50 parts by mass of main agent 2, 365 parts by mass of filler 2 and 1.53 parts by mass of filler 3 were added, and the resulting mixture was sufficiently mixed with a vacuum mixer. Subsequently, 50 parts by mass of curing agent 2 was added thereto and mixed well to obtain mixture 3.

Mixture 3 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 3. Block 3 had a density of 2.27 g/cm$^3$. Block 3 was cut into cubes each having a side length of 1 cm, and roughly pulverized at room temperature with the cutter mill. Thereafter, the resulting product was finely pulverized with the pin mill using a screen of 0.5 mm at a rotation speed of 2800 rpm. Finally, the resulting product was sieved with the circular vibrating screener (mesh size 212 μm) to obtain composite particles 3 which were thermally conductive particles. As a result of measuring the number average particle size in a similar manner to the composite particles 1, the number average particle size was 253 μm.

1-4. Composite Particles 4

To 50 parts by mass of main agent 2, 153 parts by mass of filler 2 and 3.96 parts by mass of filler 3 were added, and the resulting mixture was sufficiently mixed with a vacuum mixer. Subsequently, 50 parts by mass of curing agent 2 was added thereto and mixed well to obtain mixture 4.

Mixture 4 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 4. Block 4 had a density of 1.40 g/cm$^3$. Block 4 was cut into cubes each having a side length of 1 cm, and roughly pulverized at room temperature with the cutter mill. Thereafter, the resulting product was finely pulverized with the pin mill using a screen of 0.5 mm at a rotation speed of 2800 rpm. Finally, the resulting product was sieved with the circular vibrating screener (mesh size 212 μm) to obtain composite particles 4 which were thermally conductive particles. As a result of measuring the number average particle size in a similar manner to the composite particles 1, the number average particle size was 220 μm.

1-5. Composite Particles 5

To 50 parts by mass of main agent 2, 153 parts by mass of filler 2 and 3.96 parts by mass of filler 3 were added, and the resulting mixture was sufficiently mixed with a vacuum mixer. Subsequently, 50 parts by mass of curing agent 2 was added thereto and mixed well to obtain mixture 5.

Mixture 5 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 5. Block 5 had a density of 1.02 g/cm$^3$. Block 5 was cut into cubes each having a side length of 1 cm, freeze-pulverized, and finally sieved with the circular vibrating screener (mesh size 212 nm) to obtain composite particles 5 which were thermally conductive particles. As a result of measuring the number average particle size in a similar manner to the composite particles 1, the number average particle size was 254 μm.

In the freeze pulverization, the composite particles are cooled to a temperature equal to or lower than an embrittlement point in a liquid nitrogen (about −196° C.) atmosphere, and then pulverization can be performed using an impact type pulverizer such as a turbo mill, a pin mill, a hammer mill, or a Linrex mill.

1-5. Composite Particles 6

To 100 parts by mass of main agent 2, 175 parts by mass of filler 2 and 1.30 parts by mass of filler 3 were added, and the resulting mixture was sufficiently mixed with a vacuum mixer. Subsequently, 10 parts by mass of curing agent 2 was added thereto and mixed well to obtain mixture 6.

Mixture 6 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 6. Block 6 had a density of 1.69 g/cm$^3$. Block 6 was cut into cubes each having a side length of 1 cm, and roughly pulverized at room temperature with the cutter mill. Thereafter, the resulting product was finely pulverized with the pin mill using a screen of 0.5 mm at a rotation speed of 2800 rpm. Finally, the resulting product was sieved with the circular vibrating screener (mesh size 212 μm) to obtain composite particles 6 which were thermally conductive particles. As a result of measuring the number average particle size in a similar manner to the composite particles 1, the number average particle size was 233 μm.

1-5. Composite Particles 7

To 50 parts by mass of main agent 2, 365 parts by mass of filler 2, 1.53 parts by mass of filler 3, and 50 parts by mass of particles 1 were added, and the resulting mixture was sufficiently mixed with a vacuum mixer. Subsequently, 50 parts by mass of curing agent 2 was added thereto and mixed well to obtain mixture 7.

Mixture 7 was put into a die of 100 mm×100 mm×30 mm, was allowed to stand under vacuum at room temperature for three hours at a pressure of 4.9 MPa (50 kg/cm$^2$) with a vacuum electrothermal press machine, and then was heated at 50° C. for three hours to prepare block 7. Block 7 had a density of 2.35 g/cm$^3$. Block 7 was cut into cubes each having a side length of 1 cm, and roughly pulverized at room temperature with the cutter mill. Thereafter, the resulting product was finely pulverized with the pin mill using a screen of 0.5 mm at a rotation speed of 2800 rpm. Finally, the resulting product was sieved with the circular vibrating screener (mesh size 212 μm) to obtain composite particles 7 which were thermally conductive particles. As a result of measuring the number average particle size in a similar manner to the composite particles 1, the number average particle size was 252 μm.

Table 1 illustrates the content, density, and number average particle size of each of components forming composite particles 1 to 7 described above.

TABLE 1

| | Elastomer | | | | Filler | | | | Thermally conductive particle | | Density g/cm³ | Number average particle size μm |
|---|---|---|---|---|---|---|---|---|---|---|---|---|
| | Main agent | | Curing agent | | | | | | | | | |
| | Kind | Parts by mass | Kind | Parts by mass | Kind | Parts by mass | Kind | Parts by mass | Kind | Parts by mass | | |
| Composite particle 1 | Main agent 1 | 100 | Curing agent 1 | 10 | Filler 1 | 803 | — | — | — | — | 4.07 | 112 |
| Composite particle 2 | Main agent 2 | 50 | Curing agent 2 | 50 | Filler 2 | 365 | Filler 3 | 0.91 | — | — | 2.29 | 245 |
| Composite particle 3 | Main agent 2 | 50 | Curing agent 2 | 50 | Filler 2 | 365 | Filler 3 | 1.53 | — | — | 2.27 | 253 |
| Composite particle 4 | Main agent 2 | 50 | Curing agent 2 | 50 | Filler 2 | 153 | Filler 3 | 3.96 | — | — | 1.40 | 220 |
| Composite particle 5 | Main agent 2 | 50 | Curing agent 2 | 50 | Filler 2 | 153 | Filler 3 | 3.96 | — | — | 1.02 | 254 |
| Composite particle 6 | Main agent 2 | 100 | Curing agent 2 | 10 | Filler 2 | 175 | Filler 3 | 1.30 | — | — | 1.69 | 233 |
| Composite particle 7 | Main agent 2 | 50 | Curing agent 2 | 50 | Filler 2 | 365 | Filler 3 | 1.53 | Particle 1 | 50 | 2.35 | 252 |

2. Preparation of Backing Material

A backing material was prepared using the following materials.

(Raw Material of Matrix Resin)

Main agent 3: Albidur EP2240 (manufactured by Evonik Industries AG, liquid epoxy resin)

Curing agent 3: jER Cure ST-12 (manufactured by Mitsubishi Chemical Corporation)

Main agent 4: jER 828 (manufactured by Mitsubishi Chemical Corporation, liquid epoxy resin)

Curing agent 4: jER Cure 113 (manufactured by Mitsubishi Chemical Corporation)

Main agent 5: PCE-751 (number average particle size: 45 to 50 μm, manufactured by Pelnox Limited, powder epoxy resin)

Main agent 6: F-246 (number average particle size: 45 μm, manufactured by Somar Corporation, powder epoxy resin)

Main agent 7: Rilsan fine powder (number average particle size: 30 μm, manufactured by Arkema K.K., powder nylon 11 resin)

(Non-Thermally Conductive Particles)

Composite particles 1: Composite particles 1 prepared above

Composite particles 3: Composite particles 3 prepared above

Composite particles 5: Composite particles 5 prepared above (Thermally Conductive Particles)

Particles 1: iGrafen-α (manufactured by ITEC Co., Ltd., multilayer graphene)

Composite particles 7: Composite particles 7 prepared above

Note that the thermally conductive material (multilayer graphene) forming particles 1 and composite particles 7 each have a thermal conductivity of 1300 W/mk.

Particles 1 had a density of 2.2 g/cm³, and composite particles 7 had a density of 2.35 g/cm³.

2-1. Backing Material 1

76.0 parts by mass of main agent 3 and 730 parts by mass of composite particles 1 were sufficiently mixed with a vacuum mixer. 24.0 parts by mass of curing agent 3 was further added thereto, and further mixed to obtain a compound.

The compound was put into a die of 100 mm×100 mm×30 mm, and allowed to stand at room temperature for four hours while being pressurized at a pressure of 9.9 MPa (100 kg/cm²) with a vacuum electrothermal press machine "OHV-H" (manufactured by Oji Machine Co., Ltd.). Thereafter, the resulting product was heated at 80° C. for three hours to obtain backing material 1.

2-2. Backing Material 2

76.0 parts by mass of main agent 3 and 97.0 parts by mass of particles 1 were sufficiently mixed with a vacuum mixer. 24.0 parts by mass of curing agent 3 was further added thereto, and further mixed to obtain a compound.

The compound was put into a die of 100 mm×100 mm×30 mm, and allowed to stand at room temperature for four hours while being pressurized at a pressure of 9.9 MPa (100 kg/cm²) with the vacuum electrothermal press machine. Thereafter, the resulting product was heated at 80° C. for three hours to obtain backing material 2.

2-3. Backing Material 3

76.0 parts by mass of main agent 4, 160.0 parts by mass of composite particles 3, and 13.8 parts by mass of particles 1 were sufficiently mixed with a vacuum mixer. 24.0 parts by mass of curing agent 4 was further added thereto, and further mixed to obtain a compound.

The compound was put into a die of 100 mm×100 mm×30 mm, and allowed to stand at room temperature for four hours while being pressurized at a pressure of 9.9 MPa (100 kg/cm²) with the vacuum electrothermal press machine. Thereafter, the resulting product was heated at 80° C. for three hours to obtain backing material 3.

2-4. Backing Material 4

75.8 parts by mass of main agent 4, 160.0 parts by mass of composite particles 3, and 35.0 parts by mass of particles 1 were sufficiently mixed with a vacuum mixer. 24.2 parts by mass of curing agent 4 was further added thereto, and further mixed to obtain a compound.

The compound was put into a die of 100 mm×100 mm×30 mm, and allowed to stand at 80° C. for one hour while being pressurized at a pressure of 9.9 MPa (100 kg/cm²) with the vacuum electrothermal press machine. Thereafter, the resulting product was heated at 150° C. for three hours to obtain backing material 4.

2-5. Backing Material 5

Into a rocking mixer RM-10 (manufactured by Aichi Electric Co., Ltd.), 100 parts by mass of main agent 5, 160.0 parts by mass of composite particles 3, and 35.0 parts by mass of particles 1 were put, and mixed for 20 minutes at a rotation speed of 19 rpm at a rocking speed of 11 rpm to obtain a powder mixture.

The powder mixture was put into a die of φ200 mm×100 mm, and heated at 150° C. for four hours while being pressurized at a pressure of 9.9 MPa (100 kg/cm$^2$) with the vacuum electrothermal press machine to obtain backing material 5.

2-6. Backing Material 6

A backing material 6 was obtained in a similar manner to the backing material 5 except that the amount of particles 1 added was changed from 35.0 parts by mass to 53.0 parts by mass.

2-7. Backing Material 7

Into a rocking mixer RM-10 (manufactured by Aichi Electric Co., Ltd.), 100 parts by mass of main agent 5, 73.0 parts by mass of composite particles 5, and 35.0 parts by mass of particles 1 were put, and mixed for 20 minutes at a rotation speed of 19 rpm at a rocking speed of 11 rpm to obtain a powder mixture.

The powder mixture was put into a die of φ200 mm×100 mm, and heated at 150° C. for four hours while being pressurized at a pressure of 9.9 MPa (100 kg/cm$^2$) with the vacuum electrothermal press machine to obtain backing material 7.

2-8. Backing Material 8

Into a rocking mixer RM-10 (manufactured by Aichi Electric Co., Ltd.), 100 parts by mass of main agent 6, 160.0 parts by mass of composite particles 3, and 53.0 parts by mass of particles 1 were put, and mixed for 20 minutes at a rotation speed of 19 rpm at a rocking speed of 11 rpm to obtain a powder mixture.

The powder mixture was put into a die of φ200 mm×100 mm, and heated at 150° C. for four hours while being pressurized at a pressure of 9.9 MPa (100 kg/cm$^2$) with the vacuum electrothermal press machine to obtain backing material 8.

2-9. Backing Material 9

Into a rocking mixer RM-10 (manufactured by Aichi Electric Co., Ltd.), 100 parts by mass of main agent 7, 160.0 parts by mass of composite particles 3, and 53.0 parts by mass of particles 1 were put, and mixed for 20 minutes at a rotation speed of 19 rpm at a rocking speed of 11 rpm to obtain a powder mixture.

The powder mixture was put into a die of φ200 mm×100 mm, and heated at 150° C. for four hours while being pressurized at a pressure of 9.9 MPa (100 kg/cm$^2$) with the vacuum electrothermal press machine to obtain backing material 9.

2-10. Backing Material 10

Into a rocking mixer RM-10 (manufactured by Aichi Electric Co., Ltd.), 100 parts by mass of main agent 5, 160.0 parts by mass of composite particles 7, and 53.0 parts by mass of particles 1 were put, and mixed for 20 minutes at a rotation speed of 19 rpm at a rocking speed of 11 rpm to obtain a powder mixture.

The powder mixture was put into a die of φ200 mm×100 mm, and heated at 150° C. for four hours while being pressurized at a pressure of 9.9 MPa (100 kg/cm$^2$) with the vacuum electrothermal press machine to obtain backing material 10.

Table 2 illustrates the content and glass transition temperature (Tg) of each of components forming backing materials 1 to 10.

TABLE 2

| Backing | Base agent | | | | Non-thermally conductive particle (Composite particle) | | Thermally conductive particle | | Thermally conductive particle (Composite particle) | | Tg (° C.) | Note |
| | Main agent | | Curing agent | | | | | | | | | |
| | Kind | Parts by mass | Kind | Parts by mass | Kind | Parts by mass | Kind | Parts by mass | Kind | Parts by mass | | |
| --- | --- | --- | --- | --- | --- | --- | --- | --- | --- | --- | --- | --- |
| 1 | Main agent 3 | 76.0 | Curing agent 3 | 24.0 | Composite particle 1 | 730 | — | — | — | — | 67 | Comparative Example |
| 2 | Main agent 3 | 76.0 | Curing agent 3 | 24.0 | — | — | Particle 1 | 97.0 | — | — | 72 | Comparative Example |
| 3 | Main agent 4 | 76.0 | Curing agent 4 | 24.0 | Composite particle 3 | 160.0 | Particle 1 | 13.8 | — | — | 118 | Comparative Example |
| 4 | Main agent 4 | 75.8 | Curing agent 4 | 24.2 | Composite particle 3 | 160.0 | Particle 1 | 35.0 | — | — | 117 | Comparative Example |
| 5 | Main agent 5 | 100.0 | — | — | Composite particle 3 | 160.0 | Particle 1 | 35.0 | — | — | 158 | Example |
| 6 | Main agent 5 | 100.0 | — | — | Composite particle 3 | 160.0 | Particle 1 | 53.0 | — | — | 155 | Example |
| 7 | Main agent 5 | 100.0 | — | — | Composite particle 5 | 73.0 | Particle 1 | 35.0 | — | — | 164 | Example |
| 8 | Main agent 6 | 100.0 | — | — | Composite particle 3 | 160.0 | Particle 1 | 53.0 | — | — | 109 | Example |
| 9 | Main agent 7 | 100.0 | — | — | Composite particle 3 | 160.0 | Particle 1 | 53.0 | — | — | 33 | Example |
| 10 | Main agent 5 | 100.0 | — | — | — | — | Particle 1 | 53.0 | Composite particle 7 | 160.0 | 162 | Example |

3. Physical Properties of Backing Material

The physical properties (acoustic impedance, attenuation ratio, thermal conductivity, and sound velocity) of each of the backing materials 1 to 10 were measured by the following methods.

3-1. Acoustic Impedance

The acoustic impedance was determined according to JIS Z2353:2003. Specifically, the sound velocity was measured using a sing-around sound velocity measuring device (manufactured by Ultrasonic Engineering Co., Ltd.) at 25° C., and the acoustic impedance was calculated according to the following formula (1).

$$\text{acoustic impedance}(Z: \text{MRayls}) = \text{density}(\rho \times 10^3 \text{ kg/m}^3) \times \text{sound velocity}(C \times 10^3 \text{ m/sec}) \quad \text{Formula (1)}$$

3-2. Attenuation Ratio

The attenuation ratio of an ultrasonic wave was determined according to JIS Z2354:2012. Specifically, a water tank was filled with water at 25° C. Using an ultrasonic pulser/receiver "JPR-10C" (manufactured by Japan Probe Co., Ltd.), an ultrasonic wave of 1 MHz was generated in water, and the magnitude of an amplitude was measured before and after the ultrasonic wave passed through the sheet.

3-3. Thermal Conductivity

The thermal conductivity was determined by a laser flash method according to JIS R1611:2010. Specifically, the thermal conductivity of each of backing materials 1 to 10 (size of test piece: φ10 mm, t=2 mm) was measured with LFA-502 (manufactured by Kyoto Electronics Manufacturing Co., Ltd.).

3-4. Sound Velocity

The sound velocity was calculated according to the formula (1) using the above-described value of the acoustic impedance (Z: Mrayls) determined according to JIS Z2353:2003.

Table 3 illustrates the physical properties of each of backing Formula (1) materials 1 to 10.

backing materials 5 to 10 each have a high attenuation ratio of an ultrasonic wave, and therefore can suppress the reflection of an ultrasonic wave transmitted to a back surface side. This makes it possible to obtain a high-quality tomographic image.

Figure 4A:
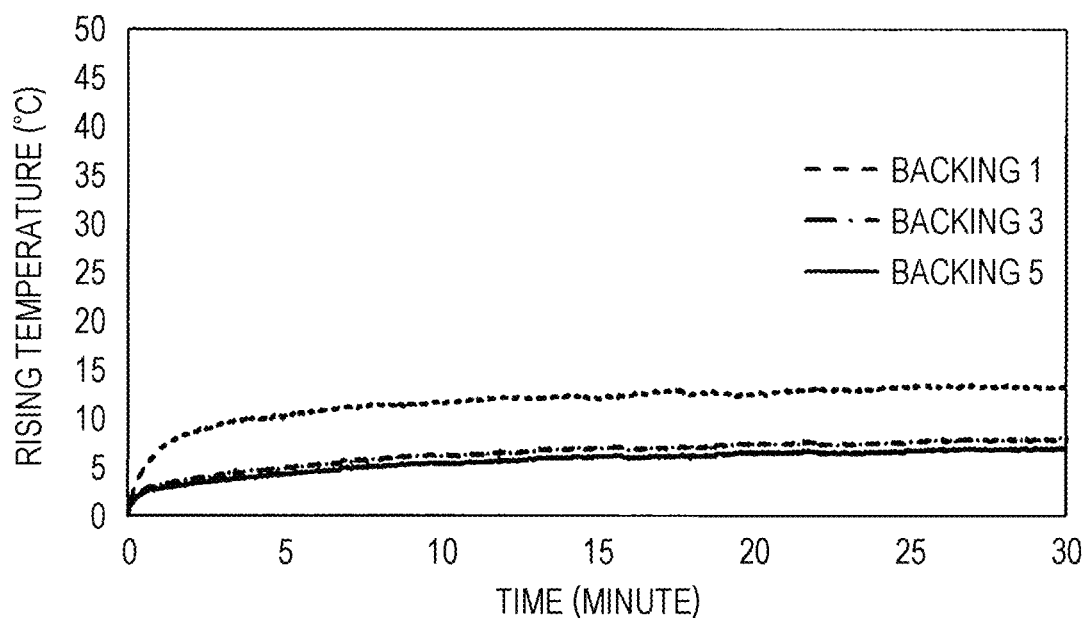
FIGS. 4A and 4B are graphs illustrating a heat dissipation effect of the ultrasonic probe according to the embodiment of the present invention.
Figure 4B:
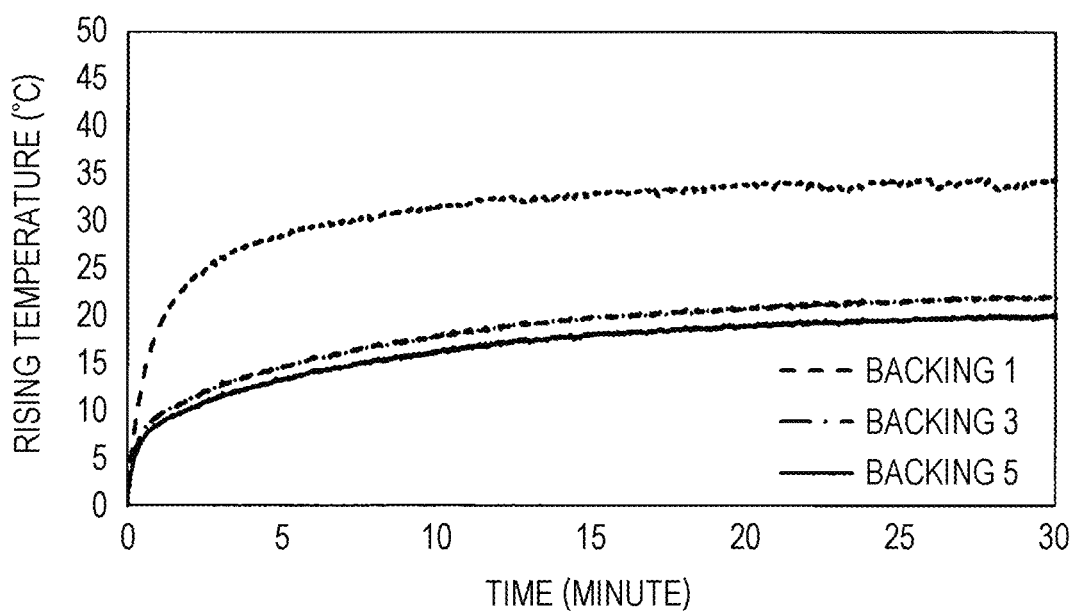

FIG. 4A is a graph illustrating heat dissipation effects of backing materials 1, 3 and 5 when an input voltage is 60 Vpp. FIG. 4B is a graph illustrating heat dissipation effects of backing materials 1, 3 and 5 when the input voltage is 100 Vpp. Note that the rising temperature of the acoustic lens illustrated in FIGS. 4A and 4B indicates a value obtained by measurement using a thermography "FLIRC2" (manufactured by FLIR Systems, Inc.).

It is found from FIGS. 4A and 4B that use of the backing material according to the embodiment of the present invention reduced heat generation of the acoustic lens even when a high voltage was applied. It is considered that this is because the amount of the thermally conductive particles used can be reduced by forming the thermally conductive particles into composite particles.

(Processability of Backing Material)

Backing materials 1 to 10 were evaluated for moldability, durability, and dicing property.

TABLE 3

| | | | Physical properties | | | | | | |
|---|---|---|---|---|---|---|---|---|---|
| | | | Thermal conductivity (W/mk) | | | Sound velocity (m/s) | | | |
| Backing | Acoustic impedance (MRayls) | Attenuation ratio (dB/min · MHz) | Thickness direction | Horizontal direction | Thickness direction/ Horizontal direction | Thickness direction | Horizontal direction | Thickness direction/ Horizontal direction | Note |
| 1 | 2.76 | 8.4 | 0.5 | 0.5 | 1.00 | 1043 | 1039 | 1.00 | Comparative Example |
| 2 | 4.06 | 3.6 | 6.3 | 6.4 | 0.98 | 1950 | 1970 | 0.99 | Comparative Example |
| 3 | 2.60 | 6.0 | 3.1 | 3.0 | 1.03 | 1433 | 1440 | 1.00 | Comparative Example |
| 4 | 2.57 | 7.8 | 4.3 | 4.5 | 0.96 | 1431 | 1424 | 1.00 | Comparative Example |
| 5 | 2.54 | 11.0 | 25.0 | 4.6 | 5.43 | 1201 | 1895 | 0.63 | Example |
| 6 | 2.69 | 15.0 | 29.9 | 6.5 | 4.60 | 1185 | 1789 | 0.66 | Example |
| 7 | 1.75 | 13.5 | 26.5 | 5.2 | 5.10 | 1385 | 2005 | 0.69 | Example |
| 8 | 2.64 | 11.0 | 29.9 | 6.5 | 4.60 | 1245 | 1846 | 0.67 | Example |
| 9 | 2.60 | 11.0 | 25.4 | 4.8 | 5.30 | 1220 | 1806 | 0.67 | Example |
| 10 | 2.71 | 9.7 | 30.2 | 6.8 | 4.44 | 1153 | 1735 | 0.66 | Example |

It was found that backing materials 5 to 10 each containing a powder base material exhibited higher attenuation ratios than backing materials 1 to 4 each containing a liquid epoxy resin. It is considered that this is because the orientation of the particles could be easily controlled by forming the thermally conductive particles into composite particles. This makes it possible to obtain a high attenuation ratio even when the content of the thermally conductive particles is reduced. Here, the larger the attenuation ratio of the backing material is, the less the reflection of an ultrasonic wave from a back surface side of a piezoelectric body is. Therefore, deterioration of a diagnostic image can be suppressed.

By changing the matrix resin used from a liquid epoxy resin to a powder epoxy resin, it was possible to obtain a backing material having a high attenuation ratio and high thermally conductive performance as illustrated in backing materials 5 to 10. Backing materials 5 to 10 can efficiently dissipate heat generated by a piezoelectric element due to a high thermal conductivity, and therefore can suppress overheat of an acoustic lens in contact with a subject. In addition, (Moldability)

Evaluation was performed using backing materials 1 to 10 molded into a diameter of 50 mm and a height of 20 mm by the above-described method.

(Evaluation Method)

Backing materials 1 to 10 were cut with a wire saw "CS-203" (manufactured by Musashino Denshi, Inc.) and further polished to a thickness of 10 mm with a precision polishing device "MA-200" (manufactured by Musashino Denshi, Inc.). The resulting backing materials 1 to 10 were observed with an optical microscope and visually, and bubbles and cracks thereof were checked. Note that evaluation criteria of A and B were acceptable.

(Evaluation Criteria)

A: No bubble or crack is generated, and no uneven distribution of particles is observed B: The number of bubbles and cracks is less than 3, and no uneven distribution of particles is observed C: The number of bubbles and cracks is less than 6, and uneven distribution of some particles is observed D: The number of bubbles and cracks is 6 or more, and uneven distribution of particles is observed (Durability)

Each of backing materials 1 to 10 prepared by the above-described method was cut into a size of 30 mm 30 mm×1 mm. Using this product as a test piece, the test piece was immersed in oleic acid at 50° C., and a swelling condition thereof was checked. Note that evaluation criteria of A and B were acceptable.

(Evaluation Criteria)

A: Swelling degree is less than 3%
B: Swelling degree is 3% or more and less than 5%
C: Swelling degree is 5% or more and less than 10%
D: Swelling degree is 10% or more (Dicing Property)

A matching layer, a piezoelectric material, a flexible printed circuit board (FPC), a backing material, and the like are bonded to each other into a TD shape. By dicing the resulting product with a 20 μm blade at a 50 μm pitch with an aspect ratio of about 6 (total 300 μm film thickness), 500 pieces were prepared. Among the 500 pieces, the number of pieces whose capacity had been changed from a theoretical value was checked. Note that evaluation criteria of A, B, and C were acceptable.

(Evaluation Criteria)

A: less than 3/500
B: less than 10/500
C: less than 200/500
D: 200/500 or more

Table 4 illustrates the moldability, durability, and dicing property of each of backing materials 1-10.

TABLE 4

| Backing | Processability | | | Note |
| --- | --- | --- | --- | --- |
| | Moldability | Durability | Dicing property | |
| 1 | A | C | A | Comparative Example |
| 2 | D | D | C | Comparative Example |
| 3 | A | A | B | Comparative Example |
| 4 | C | B | A | Comparative Example |
| 5 | A | A | A | Example |
| 6 | A | A | A | Example |
| 7 | B | A | A | Example |
| 8 | A | A | A | Example |
| 9 | A | B | A | Example |
| 10 | A | A | A | Example |

By using a powder resin as a raw material of the matrix resin, it was possible to obtain a backing material having excellent moldability, durability, and dicing property. It is considered that this is because by using powder particles as a raw material of the matrix resin, due to an excluded volume effect of particles such as the thermally conductive particles contained in the backing material, the thermally conductive particles can be oriented at regular intervals even if the thermally conductive particles are not uniformly dispersed at the time of mixing. Furthermore, it is considered that this is because by pressurization during molding, the orientation of the thermally conductive particles can be improved.

The ultrasonic probe according to the embodiment of the present invention has high heat dissipation by the backing material and little deterioration in image quality due to increased thermally conductive performance of the backing material, therefore makes it possible to perform imaging at a higher voltage, and is useful as an ultrasonic probe of an ultrasonic diagnostic apparatus having higher sensitivity.

Although embodiments of the present invention have been described and illustrated in detail, the disclosed embodiments are made for purposes of illustration and example only and not limitation. The scope of the present invention should be interpreted by terms of the appended claims.

What is claimed is:

1. A method for manufacturing a backing material used for an ultrasonic probe, the method comprising:
    mixing a raw material of a matrix resin, thermally conductive particles, and non-thermally conductive particles to prepare a mixture; and
    molding the mixture while the mixture is pressurized and heated to form a backing material, wherein
    the thermally conductive particles are made of a thermally conductive material and a number average particle size of the thermally conductive particles is 10 μm to 150 μm,
    the thermally conductive particles are oriented in a thickness direction of the backing material,
    the raw material of the matrix resin contains powder resin particles, and
    a ratio of thermal conductivity of the backing material in the thickness direction to the thermal conductivity of the backing material in a horizontal direction is 3 or more.

2. The method for manufacturing a backing material according to claim 1, wherein a ratio of sound velocity of the backing material in the thickness direction to the sound velocity of the backing material in a horizontal direction is 0.5 or more.

3. The method for manufacturing a backing material according to claim 1, wherein the raw material of the matrix resin contains powder particles having a number average particle size of 10 μm or more and 200 μm or less.

* * * * *